US005736595A

United States Patent [19]

Günther et al.

[11] Patent Number: 5,736,595
[45] Date of Patent: *Apr. 7, 1998

[54] POLYMER COMPOSITION, ABSORBENT MATERIAL COMPOSITION, THEIR PRODUCTION AND THEIR USE

[75] Inventors: Uwe Günther, Tönisvorst; Helmut Klimmek, Krefeld; Helmut Brüggemann, Duisburg, all of Germany

[73] Assignee: Chemische Fabrik Stockhausen GmbH, Krefeld, Germany

[*] Notice: The term of this patent shall not extend beyond the expiration date of Pat. No. 5,721,295.

[21] Appl. No.: 535,070

[22] PCT Filed: May 3, 1993

[86] PCT No.: PCT/EP93/01062

§ 371 Date: Nov. 3, 1995

§ 102(e) Date: Nov. 3, 1995

[87] PCT Pub. No.: WO94/25521

PCT Pub. Date: Nov. 10, 1994

[51] Int. Cl.$^6$ .............. C08L 1/26; C08L 3/08; C08L 5/00
[52] U.S. Cl. .............. 524/45; 524/44; 524/43; 524/47; 524/55; 524/35; 524/28
[58] Field of Search ............... 524/56, 43–45, 524/47, 55, 312, 310, 405, 394, 398–399, 400, 13, 28, 50, 35, 42, 57; 424/461, 462, 469, 484; 523/124, 126, 128; 604/358, 365, 367, 372, 374

[56] References Cited

U.S. PATENT DOCUMENTS

| 4,373,036 | 2/1983 | Chang et al. | 524/43 |
| 4,952,550 | 8/1990 | Wallach et al. | 502/315 |
| 5,264,471 | 11/1993 | Chmelir | 524/35 |

Primary Examiner—Peter A. Szekely
Attorney, Agent, or Firm—Foley & Lardner

[57] ABSTRACT

A polymer composition, a process for the production of a polymer composition, in particular of an absorbent, are disclosed which substantially consist of a special component A based on renewable polysaccharide raw materials, a special component B consisting of a water-soluble polymer, a matrix material, an ionic and/or covalent cross-linking agent, or an anti-blocking agent, which is obtainable in that the water-swellable polymer is brought together with the polysaccharide polymer, that these are dried and ground then, the other components are added, and mixing up to homogeneity is effected followed by a heat treatment, and that during the addition of the cross-linking agent, after said heat treatment, the same is optionally fixed by the matrix by means of a final heat treatment.

Additionally the use of this polymer composition and (animal) hygiene items and chemico-technical products are disclosed which comprise a previously manufactured polymer composition.

38 Claims, No Drawings

POLYMER COMPOSITION, ABSORBENT MATERIAL COMPOSITION, THEIR PRODUCTION AND THEIR USE

The present invention relates to polymer material compositions and to the production of a polymer composition and in particular absorbing materials mainly based on renewable raw materials. For this reason they are biodegradable in principle. Owing to the mainly native origin the absorbents do not comprise residual monomers, or considerably lower amounts thereof, as compared with absorbers based on polyacrylate. The absorbers according to the present invention have a comparatively high absorption capacity and absorption rate, also under load, for water and aqueous solutions, no tendency to gel blocking (gel blocking: on contact with water the outer layers of the absorber stick together and prevent further advancement of the liquid into the absorber), and they are mechanically stable (with respect to the separation into the individual components). In swollen condition they separate into individual particles; they are non-aqueous and have a very high gel stability. The present invention further relates to a process for their production and to their use as fiber, film, powder, or granular material for the absorption of water, aqueous solutions or aqueous dispersions and body fluids in hygiene articles, such as tampons or diapers, in animal hygiene articles, in technochemical products, for example, packaging materials, in particular for meat and fish, in culture pots, as well as in soil conditioning and as cable sheathings.

Most of the absorbing materials used today, also referred to as superabsorbers, which are capable of absorbing large amounts of liquid (water, urine) within a short period of time, primarily are slightly cross-linked polyacrylates; therefore they are not based on renewable raw materials and their biodegradability is comparatively insufficient or they are not biodegradable at all.

Endeavoring to build up superabsorbers of renewable raw materials, acrylic acid was grafted on polysaccharides, for example on corn starch, as is described in DE-PS 2612846. However, only small amounts of polysaccharides (up to a maximum of 25%) may be used, since otherwise the absorption properties will deteriorate dramatically.

By incorporating polysaccharides into the polymerization gel of polyacrylates, as is described in DE-OS 40 29 591, 40 29 592, and 40 29 593, the polyacrylates can also only be replaced to the extent of a maximum of 25%, without resulting in a clear deterioration of the absorption capacity and other properties of the resulting superabsorbers, even if various auxiliary agents are added additionally, such as fibers and, for example, aluminum cross-linkers. The polysaccharides are considered to be fundamental elements for the absorbers to obtain biodegradable units.

DE-PS 3132976 describes the mixing of polyacrylic acid with polysaccharides in powdery form and in solution, wherein the shell of the absorber particles of the mixtures are cross-linked with aluminum cross-linking agents, such as $Al(OH)_2OOCCH_3*1/3H_3BO_3$. Thus, this process cannot provide superabsorbers consisting by more than 60% of renewable raw materials.

According to the processes described in the art, the polysaccharides do not contribute much as an absorption component.

Various publications, such as DE-OS 2634539, describe the production of carboxymethylcellulose-absorbers, i.e., of materials which are biodegradable in principle, by cross-linking the carboxymethylcellulose with various cross-linking agents in aqueous system. However, these absorbers show severe gel blocking. U.S. Pat. No. 4,959,341 describes the production of an absorber based on carboxymethylcellulose, which consists of a mixture of carboxymethylcellulose, cellulose fibers, a hydrophobic component, and $Al(OH)_2OOCCH_3*1/3H_3BO_3$ as cross-linking agent, the aluminum cross-linking agent causing a cross-linkage of the carboxymethylcellulose during the liquid absorption. These absorbers have good absorption properties, however, show blocking phenomena. Additionally, these absorbers can easily be separated by mechanical stress, such as sieving or conveying, so that they are no longer present as a homogeneous product, this restricts their applicability to a great extent.

EP-PS 0 201 895 also describes the production of an absorber based on carboxymethylcellulose. However, in the production of these absorbers an aqueous solution is used in which the carboxymethylcellulose is present in a low concentration. Additionally, larger amounts of organic solvents, such as acetone, methanol, and the like are required in the production. The production of these carboxymethylcellulose-absorbers is very time-consuming. The absorbers themselves show blocking phenomena and have a low gel strength.

Initially, only the very high swelling capacity on contact with a liquid, also referred to as free swelling capacity, had been the main factor in the development of superabsorbers; later it turned out, however, that not only the amount of absorbed liquid is of importance but also the gel strength. However, absorbency, also referred to as swellability or free swelling capacity, on the one hand, and gel strength of the cross-linked polymer on the other hand, represented contrary properties, as is known by U.S. Pat. No. 3,247,171 (DOW/WALKER) and US-PS Re 32,649. This means that polymers having a particularly high absorbency exhibit a poor strength of the swollen gel so that the gel is deformable under an exerted pressure (e.g., load of a body) and further liquid distribution and liquid absorption is prevented. According to US-PS Re 32,649 a balanced relation between absorption capacity (gel volume) and gel strength should be aimed at so as to ensure liquid absorption, liquid transport, dryness of the diaper and the skin when these superabsorbers are used in a diaper construction. In this connection, not only is the polymer's capability of retaining a liquid under subsequent pressure, after swelling freely first, of importance, but also the fact that liquids are absorbed even against a simultaneously acting pressure, i.e., during the liquid absorption. This is the case in practice when a baby or person sits or lies on a sanitary article or when shear forces are acting, e.g., by movements of legs. In EP-A-0 339 461, pages 5 to 7, this specific absorption property is referred to as absorption under load ("AUL").

It was the object of the present invention to provide and produce a polymer composition, in particular an absorber, which does not have the drawbacks described above and has the following properties:

a) The absorber shall mainly consist of components of a native origin and thus be biodegradable in principle.

b) The absorbers shall have a high mechanical strength, they must not separate into their individual components during sieving or, for example, in a helical screw feeder.

c) The absorbers shall have a comparatively high absorption rate and absorption capacity for water and aqueous solutions.

d) The content of residual monomers shall be considerably lower than in conventional absorbers based on polyacrylates.

e) The absorbers shall have a very high gel stability in swollen condition; in this connection the absorber particles shall be present in the form of separated, individual particles.

f) They must not show a tendency to gel blocking.

g) The absorbers shall have a high absorption rate and absorption capacity under load for water and aqueous solutions.

Another object is the provision of an active substance containing-composition, its production and use.

According to the present invention the solution of the first object is achieved by a polymer composition and a process for the production of a polymer composition, in particular an absorbing material, substantially consisting of four components:

a component A based on reproductive special raw materials, a component B consisting of a special water-swellable polymer, a matrix material, and an ionic or covalent cross-linking agent, optionally, of an anti-blocking agent.

The present invention relates to a polymer composition, in particular an absorbent material composition, substantially consisting of 70–99.99%-wt. of a component A based on water-soluble and/or water-swellable polymers based on polysaccharides and their derivatives which have optionally been modified by cross-linkage, and 0.01–30%-wt. of a component B based on water-swellable, synthetic polymers and/or copolymers based on (meth-) acrylic acid, (meth-) acrylonitrile, (meth-) acrylamide, vinyl acetate, vinyl pyrrolidone, vinyl pyridine, maleic acid (-anhydride), itaconic acid (-anhydride), fumaric acid, vinyl sulfonic acid, and/or 2-acrylamido-2-methylpropane sulfonic acid, as well as the amides, N-alkyl derivatives, the N,N'-dialkyl derivatives, hydroxyl group-containing esters and amino group-containing esters of these polymerizable acids, with 0–98% of the acid groups of these acids being neutralized, and these polymers and/or copolymers being cross-linked by an at least bifunctional compound, used as polymer components, and 0.1–30%-wt., relative to these polymer components, of a matrix material having a melting or softening point of below 180° C. for the prevention of separation and gel blocking, 0.001–10%-wt., relative to these polymeric components, of an ionic or covalent cross-linking agent, and optionally 0–50%-wt., relative to these polymer components, of at least one anti-blocking agent based on natural and/or synthetic fibers and/or large-surface materials, obtainable by bringing together component B with component A in aqueous medium, subsequent drying and grinding, adding the further components, mixing up to homogeneity, and carrying out a heat treatment, and during the addition of the cross-linking agent after said heat treatment optionally carrying out a final heat treatment to fix the cross-linking agent with the matrix.

The present invention therefore further relates to a process for the production of a polymer composition, in particular an absorbent material, substantially consisting of 70–99.99%-wt. of a component A based on water-soluble and/or water-swellable polymers based on polysaccharides and their derivatives which have optionally been modified by cross-linkage, and 0.01–30%-wt. of a component B based on water-swellable, synthetic polymers and/or copolymers based on (meth-) acrylic acid, (meth-) acrylonitrile, (meth-) acrylamide, vinyl acetate, vinyl pyrrolidone, vinyl pyridine, maleic acid (-anhydride), itaconic acid (-anhydride), fumaric acid, vinyl sulfonic acid, and/or 2-acrylamido-2-methylpropane sulfonic acid, as well as the amides, N-alkyl derivatives, the N,N'-dialkyl derivatives, hydroxyl group-containing esters and amino group-containing esters of these polymerizable acids, with 0–98% of the acid groups of these acids being neutralized, and these polymers and/or copolymers being cross-linked by an at least bifunctional compound, used as polymer components, and 0.1–30%-wt., relative to these polymer components, of a matrix material having a melting or softening point of below 180° C. for the prevention of separation and gel blocking, 0.001–10%-wt., relative to these polymeric components, of an ionic or covalent cross-linking agent, and optionally 0–50%-wt., relative to these polymer components, of at least one anti-blocking agent based on natural and/or synthetic fibers and/or large-surface materials, characterized in that it is obtained by bringing component B together with component A in aqueous medium, subsequent drying and grinding, adding the other components, mixing up to homogeneity, and carrying out a heat treatment, and during the addition of said cross-linking agent after said heat treatment optionally fixing the cross-linking agent with the matrix by means of carrying out a final heat treatment.

Most surprisingly, it was found that in the production a slight addition of component B to component A results in a distinct improvement in the absorption properties. Since only slight additions of component B are required, the residual monomer content, e.g., of acrylic acid, of such an absorber is clearly lower than that of absorbers based on polyacrylates. The incorporation of component B into component A is achieved, for instance, by joint swelling in water or an aqueous solution and subsequent drying. Most surprisingly, this method results in a clear increase of the AUL-value; additionally, the portion of component B can surprisingly be reduced to a considerable extent, without impairing the absorption properties of the product. Furthermore, it was surprisingly found that through the addition of a solid matter, which serves as a matrix for the absorber system, in combination with the polymer absorbent, a mixture of the components A and B, and an ionic cross-linking agent, an absorbent can be produced which has a high absorption rate and absorption capacity for water and aqueous solutions as well as an improved mechanical strength with respect to separation of the individual dry particles. Additionally, the gels of this absorber system are present separately in individual particles.

Most surprisingly, these absorbers, in addition to the above-mentioned properties, additionally have a gel strength that is considerably higher than that of absorbers built up on a polyacrylic acid basis.

Water-soluble and water-swellable polymers based on polysaccharides and their derivatives are suitable as component A, such as guar, carboxymethyl guar, xanthan, alginates, gum arabic, hydroxyethylcellulose or hydroxypropylcellulose, carboxymethylcellulose and other cellulose derivatives, starch and starch derivatives, such as carboxymethyl starch and mixtures of the individual polysaccharides. The preferred polymers are guar as well as the anionic derivatives of starch, guar and cellulose, with carboxymethylcellulose representing a particularly preferred material.

The listed polymers of component A may be modified by a cross-linkage in order to reduce their solubility in water and to achieve better swelling properties. The cross-linking may take place both in the whole polymer or only on the surface of the individual polymer particles.

The reaction of the polymers may be effected with ionic cross-linkers, for example, calcium, aluminum, zircon, iron (III), and titanium compounds. The reaction may also be effected with polyfunctional carboxylic acids, such as citric acid, mucic acid, tartaric acid, malic acid, malonic acid, succinic acid, glutaric acid, adipic acid, with alcohols, such as polyethylene glycols, glycerol, pentaerythritol, propanediols, saccharose, with carbonic acid esters, such as ethylene and propylene carbonate, with amines, such as polyoxypropylene amines, with epoxy compounds, such as ethylene glycol diglycidyl ether, glycol diglycidyl ether or glycol triglycidyl ether and epichlorohydrin, with acid anhydrides, such as succinic anhydride and maleic anhydride, with aldehydes and polyfunctional (activated) olefins, such as bis-(acrylamido)-acetic acid and methylene bisacrylamide. As a matter of fact, also suitable are derivatives of the mentioned compound classes as well as heterofunctional compounds with different functional groups of the above-mentioned compound classes.

Suitable as component B are water-swellable synthetic polymers or copolymers primarily based on (meth-) acrylic acid and also based on (meth-) acrylonitrile, (meth-) acrylamide, vinyl acetate, vinyl pyrrolidone, vinyl pyridine, maleic acid, maleic anhydride, itaconic acid, itaconic acid anhydride, fumaric acid, vinyl sulfonic acid, 2-acrylamido-2-methylpropane sulfonic acid, as well as the amides, their N and N,N'-dialkyl derivatives, hydroxyl group-containing esters and amino group-containing esters of the polymerizable acids. Cross-linked, partially neutralized polyacrylates are preferred.

Up to 98%, preferably 50–80%, of the acid groups may be neutralized.

The polymers may be cross-linked by an at least bifunctional cross-linking agent.

The production of above polymers is effected according to known processes (DE-PS 27 06 135, DE-OS 40 15 085). Polyacrylates, e.g., the FAVOR®-types manufactured by Chemische Fabrik Stockhausen GmbH, represent a particularly preferred material as component B.

The components A and B may either be combined chemically, i.e., via ester bonds or by one of the listed cross-linking agents, or physically, i.e., in the sense of an interpenetrating network (IPN).

Organic solid substances melting or softening below 180° C. and preferably having a soft consistency at room temperature are suitable as matrix, for example, triglycerol monostearate. Highly viscous liquids, such as castor oil are also suitable. For preference, polycaprolactones are suitable as the matrix, such as TONE 0230 and 0240 from Union Carbide, which may also be modified, e.g., by a reaction with maleic anhydride.

The matrix imparts a higher mechanical strength to the absorber system, presumably by chemical and/or physical interactions; this considerably reduces the separation of the individual components during transports, e.g., by means of a conveyor screw or by screening. Thereby an absorbent can be manufactured which has high absorption values and, moreover, is present as a more homogeneous and thus more effective system, after finishing or incorporation into its intended place. Additionally, embedding the absorption agent in the matrix most surprisingly results in a clear reduction or even complete elimination of gel blocking, thus ensuring a high absorption rate throughout the absorber. Furthermore, the matrix firmly fixes the cross-linking agent at the surface of the individual absorber particles. The granulation of superabsorber fine dusts by means of agglomeration auxiliary agents is described in the examples of DE-PS 37 41 157 and DE-PS 39 17 646. The products thus produced have a high absorption rate for water and aqueous solutions. However, they completely consist of polyacrylates and for this reason are poorly—if at all—biodegradable. The agglomeration agents merely have a function in the granulation of a product, but not as a matrix material.

The anti-blocking agents reduce also gel blocking; thus they cause an accelerated and improved liquid absorption and ensure that the gels are separated, i.e., are present as individual particles. As is generally known, suitable anti-blocking agents include fibrous materials and other large-surface materials (cf. DE-PS 31 41 98 and DE-PS 33 13 344).

The fibers may be natural or synthetic ones, e.g., wool, cotton, silk and cellulose fibers, or polyamide, polyester, polyacrylonitrile, polyurethane fibers, fibers of olefins and their substitution products, as well as polyvinyl alcohol fibers and their derivatives. Examples of inorganic materials include, bentonites, zeolites, aerosils, and activated carbons.

Suitable cross-linking agents are compounds converting the above-mentioned polymers into a state in which the water-solubility is reduced, the suction power improved, and the block phenomena diminished.

Metallic compounds which can interact with the functional groups of the polymers are suitable ionic cross-linking agents. Particularly preferred are magnesium, calcium, aluminum, zircon, iron, titanium, and zinc compounds which have an excellent solubility in water, such as the salts of carboxylic acids and inorganic acids. Preferred carboxylic acids are acetic acid, lactic acid, salicylic acid, propionic acid, benzoic acid, fatty acids, malonic acid, succinic acid, glutaric acid, adipic acid, citric acid, tartaric acid, malic acid, and mucic acid. Preferred inorganic anions include chlorides, bromides, hydrogensulfates, sulfates, phosphates, borates, nitrates, hydrogencarbonates, and carbonates. Additionally suitable are organic compounds comprising multivalent metals, such as actylacetonates and alcoholates, e.g., iron and zirconium acetylacetonates such as Fe(acac)$_3$, and Zr(acac)$_4$, and titanium and zirconium alcoholates of butanol and propanol such as Ti(OBu)$_4$ and Zr(o-prop)$_4$.

The water-soluble cross-linking agent causes a cross-linkage of the components A and B, both with each other and between each other, in particular at the surface, thus improving the absorption properties, as is described in DE-PS 31 32 976, DE-PS 26 09 144, and U.S. Pat. No. 4,959,341.

Suitable covalent cross-linking agents are polyfunctional carboxylic acids, alcohols, amines, epoxy compounds, carboxylic acid anhydrides, and aldehydes as well as their derivatives. Examples thereof include citric acid, mucic acid, tartaric acid, malic acid, malonic acid, succinic acid, glutaric acid, adipic acid, polyethylene glycols, glycerol, propanediols, polyoxypropylene amines, epichlorohydrin, ethylene glycol diglycidyl ether, glycol diglycidyl ether, succinic anhydride, maleic anhydride, ethylene carbonate and propylene carbonate. Also suitable are natural derivatives of the listed compounds as well as heterofunctional compounds with different functional groups of the above-mentioned compound classes.

The proportion of component A in the ratio of component A to component B amounts to 70–99.99%-wt., preferably 75–95%-wt. The portion of component B amounts to 0.01–30%-wt., preferably 5–25%-wt.

The addition of component B—even in small amounts—causes a considerable improvement in the absorption properties, in particular with respect to the suction power. As compared to a pure carboxymethylcellulose material (C.M.C.-material) a surprisingly clear improvement in the absorption properties can thereby be achieved.

The required portion of component B is considerably reduced by a processing of components A and B, for instance, in swollen condition and subsequent drying.

The amount of anti-blocking agent preferably amounts to between 0.5 and 50%-wt., particularly preferred 5 to 15%-wt., relative to components A and B.

The amount of cross-linking agent in the absorber amounts to 0.001–10%-wt., preferably 3–7%-wt., relative to components A and B.

The addition of matrix material, relative to components A and B, shall amount to between 0.1–30%-wt., preferably between 2.5 and 7.5%-wt. The matrix material prevents the absorbent from disintegrating, as is observed in pure physical mixtures, e.g., in U.S. Pat. No. 4,952,550, and it additionally prevents gel blocking.

The preferred production of the absorbent is described in the following.

Step 1) Component A and component B are physically mixed in dry form at room temperature. Then they are allowed to swell together in water or in an aqueous solution under stirring. After 15 to 360 minutes, the obtained material is dried at 40° C. to 180° C. in a drying oven. The obtained product is dried then.

Step 2) The obtained material is mixed with the anti-blocking agent and the matrix component until a homogeneous mixture results. Mixing of the components is effected in suitable mixers, such as screw mixers, fluidized bed mixers, disk mixers, or ribbon mixers. Then, a heat treatment step is carried out.

The heat treatment is effected at 25° C. to 180° C., preferably at 100° C. to 120° C. The heating time amounts to 5 to 60 minutes, preferably 20 to 40 minutes. Conventional dryers or heating furnaces or ovens (e.g., disk dryers, conveyor dryers, fluidized bed dryers, or infrared dryers) are used for the heat treatment of the product.

Step 3) Subsequently, the ionic cross-linking agent, preferably aluminum dihydroxyacetate stabilized with boric acid, is thoroughly mixed with the obtained material at room temperature until a homogeneous mixture results. For fixation purposes of the cross-linking agent by the matrix, heating to 25° C. to 180° C., preferably to 50° C. to 80° C., for 5 to 60 minutes is effected again in order to melt the matrix material.

Instead of the processing described in step 1, component A may optionally be incorporated into a swollen (e.g., with water) component B, or the component B may be incorporated into the swollen (e.g., with water) component A, or the swollen (e.g., with water) component A may be incorporated into the swollen (e.g., with water) component B, optionally under the addition of water or an aqueous solution.

After grinding (step 1 ), the product may be screened, preferably to a particle size of 90–630 μm.

The incorporation of the matrix components is preferably effected at room temperature, however, the matrix component may also be used as a melt. Prior to the thermal modification, an admixture preferably consisting of water/isopropanol may be added to the mixture in step 2, in order to have a solubilizer. Water and other admixtures of water with water-soluble organic solvents may also be used instead of the water/isopropanol-mixture. EP-PS 0 083 022 describes the cross-linkage of an absorber, which consists of polyacrylic acid, with cross-linking agents comprising at least two functional groups and being able to react with the carboxyl groups of the polyacrylate. The reaction takes place at the surface of the absorber particles. DE-PS 33 14 019 and DE-PS 35 23 617 also describe the surface cross-linkage of polyacrylates by means of cross-linking agents having at least two functional groups. In contrast to the absorbers according to the present invention, these patents only describe modifications of polyacrylates—but not of polysaccharides—in the shell, however, this does by no means result in absorbers having a sufficient biodegradability.

The incorporation of the ionic cross-linking agent may also be effected directly into the physical mixture of step 2, whereupon heating to 25° C. to 180° C., preferably to 100° C. to 120° C. is effected for 5 to 120 minutes, preferably 20 to 60 minutes. In this process the above-mentioned solvent-step may be effected either prior to or after the incorporation of the cross-linking agent.

The covalent cross-linking agent may be added to the polymer mixture as an alternative and in addition to the ionic cross-linking agent, either prior to or after the matrix addition. The covalent cross-linking agent is dissolved in a preferably optional alcohol/water-mixture and dropped into the polymer mixture under rapid stirring. The quantity of solvent amounts to between 1 and 10%, relative to the polymeric mixture. Subsequently, heating to 25° C. to 180° C. is effected for 5 to 120 minutes. Water and mixtures of water with water-soluble organic solvents may be used as solvents.

Optionally, the anti-blocking agents as well as the covalent cross-linking agent may also already the added in step 1).

The absorbent material according to the present invention has a good biodegradability, as compared to products based on polyacrylic acid, with a considerably improved absorption and suction capacity for a 0.9% solution of sodium chloride, also under load, as compared to known absorbents on a native basis, and a surprisingly very high gel strength.

| Gel strength of some absorbers according to the present invention and some commercially known absorbers | |
|---|---|
| Product name | Gel strength (10 Hz) (N/m$^2$) |
| Absorbers according to the invention | |
| superabsorber of Example 1 | ≧10000 |
| superabsorber of Example 3 | ≧10000 |
| superabsorber of Example 5 | ≧10000 |
| superabsorber of Example 7 | ≧10000 |
| superabsorber of Example 9 | ≧10000 |
| Commercially known Absorbers | |
| Product A | 2450 |
| Product B | 4200 |
| Product C | 3500 |
| Product D | 2700 |
| Product E | 4950 |
| Product F | 3700 |
| Product G | 1575 |

Products A, B, C, D, F, and G:
cross-linked, partially neutralized polyacrylates
Product E:
cross-linked, partially neutralized polyacrylate-starch-graft polymer.

Additionally, the mechanical strength (with respect to disintegration into the individual components) is considerably improved as compared to the previously described absorbers based on renewable raw materials.

The polymer composition according to the present invention may particularly be used as absorbent as a fiber, film, powder, or granular material to absorb water or aqueous liquids, such as urine and blood, and therefore is particularly suitable for the use in diapers, tampons, surgical products, cable sheathings, culture pots, packaging materials for meat or fish, and in absorbent garments.

Additionally, the material is suitable as storage medium for the gradual release of active substances, such as drugs, pesticides (U.S. Pat. Nos. 4,818,534; 4,983,389; 4,983,390; 4,985,251) and fragrances, having the advantage that the storage medium is degradable. Therefore, an additional advantage results in the fact that the active substance is released completely. The active substance-containing depot materials may be manufactured by absorption, preferably of concentrated, aqueous or hydrous solutions into the substantially dry absorber, and renewed drying, if necessary.

The active substance may also be added directly or as a solution or dispersion in any previous stage of the production process of the absorber composition.

The active substance-containing depot materials are used in the form of a powder or as a dispersion in hydrophobic media, which may comprise dispersion-stabilizing agents, such as emulsifiers or stabilizers, or in admixture with other substances, such as polysaccharides.

For instance, the addition of these bactericide-containing depot materials to cellulose, guar or starch products or their derivatives, such as carboxymethylcellulose, prevents the decomposition of these substances during storage and application in aqueous media over a longer period of time, thus avoiding larger amounts of free active substance in the solution owing to the depot effect.

Test Methods

Tea Bag Test (TBT)

To determine the absorption capacity a tea bag test was carried out. An aqueous 0.9% NaCl-solution was used as test solution. 0.2 g of a test substance (screened to between 90 and 630 µm), which had been weighed into a tea bag, was allowed to swell in the test solution for 10 and 30 minutes, respectively. After dripping for 5 minutes (maximum value), centrifuging was effected in a centrifuge, e.g., in a commercial spin dryer, at 1400 rpm. The liquid absorption was determined gravimetrically and expressed in terms of 1 g of substance (retention value).

Absorption under Load (AUL)

To determine the liquid absorption capacity under a load, the absorption under load—as described in EP-A 0 339 461 —was determined. 0.16 g test substance (screened to between 300 and 600 µm) was allowed to swell by capillary action in 0.9% NaCl-solution for 60 minutes under a pressure of 1.55 kN/m$^2$ (99.8 g/in$^2$). The liquid absorption was determined gravimetrically and expressed in terms of 1 g of substance.

Gel strength (G')

To determine the gel strength G' of the swollen absorbers the method described in EP-A 0 339 461 was used. Apparatus: Controlled Stress Rheometer CS 100, Carri-Med Ltd. Dorking/UK. Measurement conditions: Plate-plate-system, diameter 60 mm, space between plates 2 mm, temperature 20° C., torque 1000–4000 µNm, amplitude 1.5–5 mrad, frequency 10.0 Hz, 28 ml 0.9% NaCl/g absorber. The indications are given in N/m$^2$.

Flow Test (FT)

By means of the flow test the velocity at which the products absorbed the test liquid was determined; moreover, it was examined whether they showed blocking phenomena, were completely swollen and whether they were wetted all over. Furthermore, it was examined whether the gels were present in a solid, tacky or loose and separated form.

To carry out the flow test, about 100 mg of substance were placed on a water-soaked paper cloth, and the water absorption by the products was observed. The absorption behavior was evaluated according to the following graduation:

A: is absorbed rapidly

B: is absorbed very rapidly

C: is absorbed from beginning to end

D: after water absorption, gel is present in separated form

E: gel blocking.

The present invention will be illustrated in more detail in the following by means of production and application examples.

Pre-products

Each of the following mixtures are stirred into 360 ml of water at room temperature (15° to 20° C.) and allowed to stand for three hours. Subsequently, the resulting gels are dried at 100° C. in the recirculating air dryer for two hours and then ground and screened to a particle size of 90–630 µm.

Pre-product 1

38 g C.M.C. Walocel 40000 (sodium carboxymethylcellulose, product of Wolff Walsrode), 2 g of a polyacrylate superabsorber (manufactured according to DE-OS 40 15 085, example 4, referred to "SAB A" in the following).

Pre-product 2

38 g C.M.C. (Walocel 30000), 2 g "SAB A"

Pre-product 3

36 g C.M.C. (Walocel 30000), 4 g "SAB A"

Pre-product 4

32 g C.M.C. (Walocel 30000), 8 g "SAB A"

Pre-product 5

32 g C.M.C (Walocel 30000), 8 g "SAB A", 4 g cellulose fiber (PWC 500, product of Rettenmaier).

Pre-product 6

28.5 g C.M.C. (Walocel 30000), 9.5 g guar flour (type 104, product of Roeper), 2 g "SAB A"

Pre-product 7 (comparative product)

40 g C.M.C. (Walocel 40000) without additive

EXAMPLES

Example 1

5 g of pre-product 1 is thoroughly mixed with 0.25 g (cellulose, diameter: 17 µm, length: 30 µm) fiber BE 600/30 (product of Rettenmaier), and 0.25 g acid-terminated TONE 230 is (a reaction product of TONE 230, polyol based on caprolactone, molecular weight 1250 g. mol$^{-1}$, product of Union Carbide, and maleic anhydride) and then heated in the oven to 120° C. for 30 minutes. Then 0.25 g Al(OH)$_2$OOCCH$_3$*1/3H$_3$BO$_3$ is added followed by heating to 50° C. in the oven for one hour.

TBT (max./ret.)=48 g/g / 26 g/g; AUL=18.0 g/g; FT: B C D

Example 2

5 g of pre-product 2 is thoroughly mixed with 0.25 g Aerosil R 972 (fumed silica, particle diameter: 16 nm, product of Degussa AG), 0.25 g acid-terminated TONE 230, 0.5 ml water, and 1 ml i-propanol and then heated in the oven to 120° C. for 30 minutes. Then, 0.25 g Al(OH)$_2$OOCCH$_3$*1/3H$_3$BO$_3$ is added followed by heating to 50° C. in the oven for one hour.

TBT (max./ret.)=51 g/g / 28 g/g; AUL=19.6 g/g; FT: B C D

Example 3

Procedure as in Example 2, however, pre-product 3 is used instead of pre-product 2, furthermore, Aerosil A 200

(fumed silica, particle diameter: 12 nm, Degussa AG) is used instead of Aerosil R 972.

TBT (max./ret.)=45 g/g / 27 g/g; AUL=17.0 g/g; FT: B C D

Example 4

Procedure as in Example 2, however, pure TONE 230 is used instead of acid-terminated TONE 230; furthermore, thorough mixing is effected with twice the amount of water and twice the amount of i-propanol.

TBT (max./ret.)=52 g/g / 29 g/g; AUL=19.0 g/g; FT: B C D

Example 5

Procedure as in Example 2, however, pre-product 5 is used.

TBT (max./ret.)=47 g/g / 27 g/g; AUL=18.3 g/g; FT: B C D

Example 6

Procedure as in Example 3, however, only half the amount of acid-terminated TONE 230 is used, and Aerosil A 200 is replaced by the same amount of fiber BE 600/30.

TBT (max./ret.)=52 g/g / 29 g/g; AUL=18.7 g/g; FT: B C D

Example 7

Procedure as in Example 2, however, (prior to the first heating) 0.25 g fiber BE 600/30 is additionally incorporated.

TBT (max./ret.)=49 g/g / 28 g/g; AUL=18.9 g/g; FT: B C D

Example 8

Procedure as in Example 2, however, pre-product 6 is used.

TBT (max./ret.)=38 g/g / 22 g/g; AUL=16.5 g/g; FT: A C D

Example 9

Procedure as in Example 2, however, pre-product 5 is used, and the amount of aluminum cross-linker is reduced to 0.2 g.

TBT (max./ret.)=49 g/g / 28 g/g; AUL=16.8 g/g; FT: A C D

Example 10

100 g of the product obtained in Example 1 is mixed with 100 ml of a 0.125% aqueous solution of 3,7-bis (dimethylamino)-phenothiazinium chloride and then dried at 60° C. in the recirculating air dryer for 2 h. 200 mg of the product thus obtained are placed in a tea bag. This is suspended in a beaker with 50 ml 0.2% solution of sodium chloride. After one hour, the tea bag is removed. The dye of the sodium chloride solution is assessed, then the procedure is repeated with fresh NaCl-solution. Even after the 5th cycle, the blueness of the sodium chloride solution shows the release of the active substance from the polymer composition serving as storage medium.

Example 11

In the preparation of pre-product 1, 0.05 g of 3,7-bis (dimethylamino)—phenothiazinium chloride is additionally added to the powder mixture, and the further processing is as described. According to Example 1, an absorber is prepared from this pre-product. The absorber thus prepared is examined as in Example 10. The obtained results are the same as in Example 10.

COMPARATAIVE EXAMPLES

Comparative Example 1

Procedure as in Example 2, however, pre-product 7 and half the amount of acid-terminated TONE 230 is used.

TBT (max./ret.)=36 g/g / 27 g/g; AUL=8.0 g/g; FT: E

Comparative Example 2

20 g C.M.C. 30000 is kept at 50° C. for 4 hours with 8 g isopropanol, 200 g water, 0.4 g Al(OH)$_2$OOCCH$_3$*1/3H$_3$BO$_3$, and 0.8 g acetic acid. Then drying at 80° C. follows.

TBT (max./ret.)=16 g/g / 11 g/g; AUL=8.9 g/g; FT: E

Comparative Examples 3, 4

The manufacture of the products according to Examples 3 and 5 was repeated without the addition of a matrix material. The products so obtained were inhomogeneous, could be separated by screening and blocked. With respect to the TBT and AUL-test, no reproducible values could be obtained because of the inhomogeneity of the products (separation during screening).

Comparative Example 5

60 g C.M.C. 40000 is thoroughly mixed with 1.5 g ethylene carbonate, 1.5 ml water, and 1.5 ml isopropanol followed by heating to 120° C. for 60 min. in the oven. 8 g of this product is thoroughly mixed with 2 g Favor® 953 (cross-linked, partially neutralized polyacrylate, product of Stockhausen GmbH), 0.5 g TONE 230, 0.5 g fiber BE 600/30, and 0.5 g Al(OH)$_2$OOCCH$_3$*1/3H$_3$BO$_3$ by using 2 ml isopropanol and 1 ml water, and heated to 120° C. for 60 min. in the oven.

TBT (max./ret.)=46 g/g / 29 g/g; AUL=14.4 g/g; FT: B C D

Comparative Example 6

8 g C.M.C. 40000 is thoroughly mixed with 2 g "SAB A", 0.5 g fiber BE 600/30, 0.5 g acid-terminated TONE 230, 0.1 g Aerosil R 972, 2 ml i-propanol and 1 ml water, and then heated for 30 minutes to 120° C. in the oven. 0.6 g Al(OH)$_2$OOCCH$_3$*1/3H$_3$BO$_3$ is added to the product thus obtained, followed by heating in the oven to 50° C. for one hour.

TBT (max./ret.)=51 g/g / 36 g/g; AUL=11.0 g/g; FT: B C D

We claim:

1. An absorbent polymer composition comprising:
  (A) 70–99.99%-wt. of component A, wherein said component A is a water-soluble or water-swellable polysaccharide or a polysaccharide derivative selected from the group consisting of carboxymethyl guar, hydroxyethylcellulose, hydroxypropylcellulose, carboxymethylcellulose and carboxymethyl starch, which polysaccharide or polysaccharide derivative may optionally be modified by cross-linkage, and
  (B) 0.01–30%-wt. of component B, wherein said component B is a water-swellable, synthetic polymer or copolymer of polymeric subunits selected from the group consisting of (meth-)acrylic acid, (meth-)acrylonitrile, (meth-)acrylamide, vinyl acetate, vinyl pyrrolidone, vinyl pyridine, maleic acid or anhydride, itaconic acid or anhydride, fumaric acid, vinyl sulfonic acid, 2-acrylamido-2-methylpropane sulfonic acid, and the amides, the N-alkyl derivatives, the N,N'-dialkyl derivatives, the hydroxyl group-containing esters, and the amino group-containing esters of said subunits, wherein 0–98%-wt. of any acid groups may be neutralized, and wherein said polymer or copolymer is cross-linked by an at least bifunctional compound, wherein the recited weight percentages of said components A and B are based on the total weight of components A and B, and (C) 0.1–30%-wt., relative to said polymer components A and B, of an organic matrix material having a melting or softening point, respectively, of below 180° C., wherein said matrix material prevents separation and gel blocking of said absorbent polymer composition, and (D) 0.001 to 10%-wt., relative to said two polymer components A and B, of an ionic or covalent cross-linking agent, wherein said cross-linking agent cross-links said components A and B with each other, and (E) 0–50%-wt., relative to said polymer components A and B, of at least one anti-blocking agent, wherein said absorbent polymer composition is made by a process comprising the steps of:

bringing said component B together with said component A in an aqueous medium, subsequently drying and grinding the resulting mixture, adding said matrix material (C) and said anti-blocking agent (E), mixing the resulting mixture to homogeneity, carrying out a first heat treatment, adding said cross-linking agent (D), and optionally carrying out a second heat treatment.

2. An active substance-containing composition comprising the absorbent polymer composition according to claim 1 and at least one active substance, wherein said active substance is releasable from said active substance-containing composition in a retarded manner.

3. The composition according to claim 1, wherein said composition comprises 75–95%-wt. of said component A, 5–25%-wt. of said component B, 2.5–7.5%-wt., relative to said components A and B, of at least one said organic matrix material (C), 3–7%-wt., relative to said components A and B, of at least one said ionic or covalent cross-linking agent (D), and 0.5–50%-wt., relative to said components A and B, of at least one said anti-blocking agent (E).

4. The composition according to claim 1 wherein said polysaccharide or polysaccharide derivative is selected from the group consisting of guar, starch, cellulose, carboxymethyl guar, hydroxyethylcellulose, hydroxroypropylcellulose, carboxymethylcellulose and carboxymethyl starch.

5. The composition according to claim 1 wherein the matrix material is selected from the group consisting of triglycerol monostearate, castor oil and polycaprolactones, which are optionally modified by a reaction with maleic anhydride.

6. The composition according to claim 1, wherein the ionic cross-linking agent (D) is selected from the group consisting of metallic compounds in the form of their salts with organic and inorganic acids.

7. The composition according to claim 1, wherein the covalent cross-linking agent (D) is a compound selected from the group consisting of polyfunctional carboxylic acids, alcohols, amines, epoxy compounds, carboxylic acid anhydrides, and aldehydes, and heterofunctional compounds comprising at least two functional groups of compounds selected from the group consisting of polyfunctional carboxylic acids, alcohols, amines, epoxy compounds, carboxylic acid anhydrides, and aldehydes.

8. A process for the production of an absorbent polymer composition comprising:

(A) 70–99.99%-wt. of component A, wherein said component A is a water-soluble or water-swellable polysaccharide, or a polysaccharide derivative selected from the group consisting of carboxymethyl guar, hydroxyethylcellulose, hydroxypropylcellulose, carboxymethylcellulose and carboxymethyl starch, which polysaccharide or polysaccharide derivative may optionally be modified by cross-linkage, and (B) 0.01–30%-wt. of component B, wherein said component B is a water-swellable, synthetic polymer or copolymer of polymeric subunits selected from the group consisting of (meth-)acrylic acid, (meth-)acrylonitrile, (meth-) acrylamide, vinyl acetate, vinyl pyrrolidone, vinyl pyridine, maleic acid or anhydride, itaconic acid or anhydride, fumaric acid, vinyl sulfonic acid, and 2-acrylamido-2-methylpropane sulfonic acid, and the amides, the N-alkyl derivatives, the N,N'-dialkyl derivatives, the hydroxyl group-containing esters, and the amino group-containing esters of said subunits, wherein 0–98%-wt. of any acid groups may be neutralized, and wherein said polymer or copolymer is cross-linked by an at least bifunctional compound, wherein the recited weight percentages of said components A and B are based on the total weight of components A and B, and (C) 0.1–30%-wt., relative to said polymer components A and B, of an organic matrix material having a melting or softening point, respectively, of below 180° C., wherein said matrix material prevents separation and gel blocking of said absorbent polymer composition, and (D) 0.001 to 10%-wt., relative to said two polymer components A and B, of an ionic or covalent cross-linking agent, wherein said cross-linking agent cross-links said components A and B with each other, and (E) 0–50%-wt., relative to said polymer components A and B, of at least one anti-blocking agent, which process comprises the steps of:

bringing said component B together with said component A in an aqueous medium, subsequently drying and grinding the resulting mixture, adding said matrix material (C) and said anti-blocking agent (E), mixing the resulting mixture to homogeneity, carrying out a first heat treatment, adding said cross-linking agent (D), and optionally carrying out a second heat treatment.

9. The process according to claim 8, wherein said composition comprises 75–95%-wt. of said component A, 5–25%-wt. of said component B, 2.5–7.5%-wt., relative to said components A and B, of at least one said organic matrix material (C), 3–7%-wt.; relative to said components A and B, of at least one said ionic or covalent cross-linking agent (D), and 0.5–50%-wt., relative to said components A and B, of at least one said anti-blocking agent (E).

10. The process according to claim 8, wherein said polysaccharide or polysaccharide derivative is selected from the group consisting of guar, starch, cellulose, carboxymethyl guar, hydroxyethylcellulose, hydroxypropylcellulose, carboxymethylcellulose and carboxymethyl starch.

11. The process according to claim 10 wherein the matrix material is selected from the group consisting of triglycerol monostearate, castor oil and polycaprolactones, which are optionally modified by a reaction with maleic anhydride.

12. The process according to claim 10 wherein the ionic cross-linking agent (D) is selected from the group consisting of metallic compounds, in the form of their salts with organic and inorganic acids.

13. The process according to claim 8, wherein the covalent cross-linking agent (D) is a compound selected from the group consisting of polyfunctional carboxylic acids, alcohols, amines, epoxy compounds, carboxylic acid anhydrides, and aldehydes, and heterofunctional compounds comprising at least two functional groups of compounds selected from the group consisting of polyfunctional carboxylic acids, alcohols, amines, epoxy compounds, carboxylic acid anhydrides, and aldehydes.

14. The process of claim 8, wherein said component B is mixed with said component A in an aqueous medium, said components A and B are then swollen in a hydrous solution or dispersion, and the resulting mixture is dried and ground.

15. The process according to claim 14, wherein both of said polymer components A and B are mixed in dry form or one of said components A and B in dry form is mixed with the other of said components A and B which is already swollen by means of a hydrous solution or dispersion.

16. The process according to claim 8, wherein said component B is swollen by a hydrous solution or dispersion and is mixed with said component A which is swollen by a hydrous solution or dispersion, optionally under the addition of a hydrous solution or dispersion, and wherein the resulting mixture is dried and ground.

17. The process according to claim 1, wherein the mixing of the polymer components and the mixing of the other components is effected at temperatures of 0° C. to 100° C.

18. The process according to claim 17, wherein the drying is effected at 40° C. to 180° C. and the ground product is screened to a particle size of 90 to 630 µm.

19. The process according to claim 1, wherein said first heat treatment is carried out at 25° C. to 180° C., and said optional second heat treatment is carried out at 25° C. to 180° C.

20. The process according to claim 1, wherein following the grinding, said organic matrix material and said anti-blocking agent are admixed in the presence of a hydrous solution or dispersion.

21. The process according to claim 1, wherein the cross-linking agent is dissolved or dispersed in a mixture of water and/or a hydrous organic solvent and added to the polymer components to be contacted or to the other components, prior to said first heat treatment.

22. The absorbent composition according to claim 1, wherein said composition is contained in a fiber, film, powder, or granular material.

23. A composition comprising the absorbent composition of claim 2, wherein said absorbent composition is in the form of a powder or is dispersed in hydrophobic media.

24. An active substance-containing composition according to claim 2, wherein said active substance is selected from the group consisting of a drug, a pesticide, a bactericide, and a perfume.

25. A composition according to claim 4, wherein component A is carboxymethylcellulose.

26. A composition of claim 6, wherein said metal compounds are selected from the group consisting of magnesium, calcium, aluminum, zirconium, iron, titanium, and zinc compounds.

27. A process according to claim 9, wherein said composition comprises 5–15%-wt., relative to said components A and B, of said at least one anti-blocking agent.

28. A process according to claim 10, wherein component A is carboxymethylcellulose.

29. A process according to claim 12, wherein said metal compounds are selected from the group consisting of magnesium, calcium, aluminum, zirconium, iron, titanium, and zinc compounds.

30. A process according to claim 17, wherein said mixing occurs at room temperature.

31. A process according to claim 19, wherein said first heat treatment is carried out at from 100° C. to 120° C., and said optional second heat treatment is carried out at from 50° C. to 80° C.

32. A process according to claim 20, wherein said matrix material and said anti-blocking agent are admixed in the presence of water or a mixture of water and a hydrous organic solvent.

33. An article comprising the absorbent composition of claim 22, wherein said article is selected from the group consisting of packaging materials, culture pots, cable sheathing, tampons, diapers and animal hygiene products.

34. A composition of claim 23, wherein said composition further comprises a dispersion stabilizer.

35. A process according to claim 8, further comprising the steps of contacting said absorbent polymer composition with an aqueous or hydrous solution comprising an active agent, and optionally drying the resulting mixture, thereby forming a depot material composition.

36. A process according to claim 8, further comprising the step of adding an active agent to the mixture at any of the steps, thereby forming a depot material composition.

37. The composition according to claim 1, wherein the covalent cross-linking agent (D) is a compound selected from the group consisting of citric acid, mucic acid, tartaric acid, malic acid, malonic acid, succinic acid, glutaric acid, adipic acid, polyethylene glycols, glycerol, propanediols, polyoxypropylene amines, epichlorohydrin, ethylene glycol diglycidyl ether, glycol diglycidyl ether, succinic anhydride, maleic anhydride, ethylene carbonate and propylene carbonate, and heterofunctional compounds comprising at least two functional groups of compounds selected from the group consisting of citric acid, mucic acid, tartaric acid, malic acid, malonic acid, succinic acid, glutaric acid, adipic acid, polyethylene glycols, glycerol, propanediols, polyoxypropylene amines, epichlorohydrin, ethylene glycol diglycidyl ether, glycol diglycidyl ether, succinic anhydride, maleic anhydride, ethylene carbonate and propylene carbonate.

38. The process according to claim 8, wherein the covalent cross-linking agent (D) is a compound selected from the group consisting of citric acid, mucic acid, tartaric acid, malic acid, malonic acid, succinic acid, glutaric acid, adipic acid, polyethylene glycols, glycerol, propanediols, polyoxypropylene amines, epichlorohydrin, ethylene glycol diglycidyl ether, glycol diglycidyl ether, succinic anhydride, maleic anhydride, ethylene carbonate and propylene carbonate, and heterofunctional compounds comprising at least two functional groups of compounds selected from the group consisting of citric acid, mucic acid, tartaric acid, malic acid, malonic acid, succinic acid, glutaric acid, adipic acid, polyethylene glycols, glycerol, propanediols, polyoxypropylene amines, epichlorohydrin, ethylene glycol diglycidyl ether, glycol diglycidyl ether, succinic anhydride, maleic anhydride, ethylene carbonate and propylene carbonate.

* * * * *